(12) United States Patent
König et al.

(10) Patent No.: US 8,298,152 B2
(45) Date of Patent: Oct. 30, 2012

(54) DEVICE AND METHOD FOR MONITORING AN ACCESS TO A PATIENT, IN PARTICULAR A VASCULAR ACCESS IN EXTRACORPOREAL BLOOD TREATMENT

(75) Inventors: Christoph König, Wiesbaden (DE); Wolfgang Kleinekofort, Kelkheim (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 174 days.

(21) Appl. No.: 12/440,266

(22) PCT Filed: Sep. 6, 2007

(86) PCT No.: PCT/EP2007/007763
§ 371 (c)(1),
(2), (4) Date: Mar. 6, 2009

(87) PCT Pub. No.: WO2008/028653
PCT Pub. Date: Mar. 13, 2008

(65) Prior Publication Data
US 2010/0241024 A1    Sep. 23, 2010

(30) Foreign Application Priority Data
Sep. 8, 2006 (DE) .......................... 10 2006 042 336

(51) Int. Cl.
*A61B 5/02* (2006.01)
(52) U.S. Cl. ....................................................... 600/506

(58) Field of Classification Search .................. 600/300, 600/301, 481, 504–507, 547, 561, 573, 576, 600/579
See application file for complete search history.

(56) References Cited

U.S. PATENT DOCUMENTS

| 6,663,585 | B1 | 12/2003 | Ender |
| 6,932,786 | B2 | 8/2005 | Giacomelli et al. |
| 7,060,047 | B2 | 6/2006 | Lodi et al. |
| 2003/0195454 | A1 | 10/2003 | Wariar et al. |

FOREIGN PATENT DOCUMENTS

| DE | 19739099 C1 | 1/1999 |
| WO | 01/47581 A | 7/2001 |
| WO | 02/102441 A | 12/2002 |

OTHER PUBLICATIONS

International Search Report, PCT/EP2007/007610, mailed Feb. 26, 2008.

*Primary Examiner* — Jeffrey G Hoekstra
(74) *Attorney, Agent, or Firm* — Kenyon & Kenyon LLP

(57) ABSTRACT

The present invention relates to a device and a method for monitoring an access to a patient, in particular a vascular access in extracorporeal blood treatment, in which a patient's blood is withdrawn from the patient via an arterial conduit and is returned to the patient via a venous conduit. In the device according to the present invention and in the method according to the present invention, an alternating voltage signal, relative to a common ground potential, is coupled in and out of the arterial and venous conduits, and the blood flowing through the arterial and venous conduits is at ground potential. In this way, disturbances, which can be attributed particularly to movements of the conduits, are reduced.

20 Claims, 3 Drawing Sheets

DEVICE AND METHOD FOR MONITORING AN ACCESS TO A PATIENT, IN PARTICULAR A VASCULAR ACCESS IN EXTRACORPOREAL BLOOD TREATMENT

CROSS REFERENCE TO RELATED APPLICATIONS

This is a 371 national phase application of PCT/EP2007/007763 filed Sep. 6, 2007, claiming priority to German Patent Application No. 10 2006 042 336.4 filed Sep. 8, 2006.

FIELD OF INVENTION

The present invention relates to a device and a method for monitoring an access to a patient, in which a fluid is withdrawn from the patient via a first tubular conduit, which comprises a first patient connector, and the fluid is returned to the patient via a second tubular conduit, which comprises a second patient connector. In particular, the present invention relates to a device and method for monitoring a vascular access during an extracorporeal blood treatment in which a patient's blood is withdrawn from the patient via an arterial tubular conduit, which comprises an arterial patient connector with an arterial puncture cannula, and is returned to the patient via a venous tubular conduit, which comprises a venous patient connector with a venous puncture cannula.

BACKGROUND OF THE INVENTION

In the field of medical engineering, many devices are known with which fluids can be withdrawn from a patient or delivered to a patient via a tubular conduit. The access to the patient is usually made with a catheter for insertion into organs of the body, or a cannula for puncturing vessels. During the examination or treatment, a correct access to the patient has to be ensured. It is therefore necessary to monitor the patient access.

In blood purification methods such as hemodialysis, hemofiltration and hemodiafiltration, blood is passed through an extracorporeal blood circuit. If the venous connection to the patient comes loose during the blood treatment, bleeding to death can be avoided only if the extracorporeal blood flow is stopped within a few seconds. Therefore, extracorporeal blood circuits are generally provided with protective systems which, in the event of an alarm, stop the blood pump, close the venous clamp and trigger an acoustic or optical warning signal.

DE 197 39 099 C1 describes a device for monitoring an access during an extracorporeal blood treatment, in which an electric current is induced in the connection of the extracorporeal blood circuit representing a closed conductor loop, the current flowing in the conductor loop is measured, and a characteristic change in the current strength points to an incorrect vascular access. In addition to inductive injection and output, it is also known to perform capacitive injection and output of electric signals in the extracorporeal blood circuit.

U.S. Pat. No. 6,932,786 B2 describes a monitoring device in which an AC voltage signal is capacitively injected and output in the extracorporeal blood circuit. The injection and output of the AC voltage signal takes place by means of electrical contact elements that enclose the tubular conduits. The electrical contact element in this case represents one "electrode" of a "capacitor", while the blood flowing in the tubular conduits represents the other "electrode" of the "capacitor". The insulating tubular conduit represents the dielectric of the capacitor lying between the electrodes.

In the known monitoring device, the AC voltage signal generated by an AC voltage signal generator is coupled to a venous contact element on the venous blood conduit and to an arterial contact element on the arterial blood conduit as a difference signal. In an alternative embodiment, one output of the frequency generator is connected to a contact element enclosing the venous blood conduit, while the other output of the signal generator is at ground potential. Both embodiments are based on the fact that the AC voltage signal is output as a difference signal with two contact elements that are arranged at different locations of the extracorporeal circuit, and the blood flowing in the extracorporeal circuit is at ground potential.

It has been found in tests that, in the method known from U.S. Pat. No. 6,932,786 B2, the output AC voltage signal can be superposed by relatively strong interference signals. In practice, therefore, the known device can prove relatively susceptible to faults.

US 2003/0195454 A1 deals with the problem of capacitive injection and output of measurement signals in the extracorporeal blood circuit and proposes injection and output of the measurement signals by means of electrical contact elements that are directly in contact with the blood flowing through the tubular conduits.

U.S. Pat. No. 7,060,047 describes a device for monitoring a vascular access during a dialysis treatment, which permits capacitive injection of an AC voltage signal, wherein an electrical circuit is closed via a common ground. The device in principle permits connection of the patient to ground. However, the document states that such a coupling of the patient is not absolutely essential.

SUMMARY OF THE INVENTION

It is an object of the present invention to make available a device that permits monitoring an access to a patient with a high degree of reliability, even though the measurement signal is injected and output capacitively. It is a further object of the present invention to make available a blood treatment device that comprises a device for monitoring a patient access and permits monitoring of the patient access with a high degree of reliability. It is also an object of the present invention to make available a method that permits monitoring of the access with a high degree of reliability.

The monitoring device according to the present invention and the monitoring method according to the present invention differ from the monitoring devices and monitoring methods known from the prior art in that the AC voltage signal is injected and output relative to a common ground potential. Moreover, a differential measurement does not take place. It has been surprisingly found that, with injection and output of the AC voltage signal relative to a common ground potential, it is possible to reduce the interference signals that could otherwise arise, particularly during the unavoidable movements of the tubes.

In the device according to the present invention and in the method according to the present invention, the AC voltage signal is injected only at one location of one of the two tubular conduits and is output only at one location of the other of the two tubular conduits. This also reduces the outlay for capacitive injection and output of the voltage signal.

The means for capacitive injection and output of the AC voltage signal are preferably bodies of electrically conductive material, for example metal sleeves, that enclose the tubular conduits.

An incorrect vascular access, for example due to the venous or arterial puncture cannula slipping out of the venous or arterial blood conduit, results in a change in impedance, which in turn leads to a change in the amplitude of the output AC voltage signal. Consequently, in the event of a characteristic change in the amplitude of the measured AC voltage signal, preferably a reduction in said amplitude, it can be concluded that the vascular access is not as it should be.

During extracorporeal blood treatment, an incorrect vascular access may exist not only when the arterial and/or venous puncture cannula has slipped out of the arterial or venous blood conduit, but also when the blood conduit is interrupted. The known arterial and venous blood conduits generally comprise tube couplers that interconnect two tube portions upstream and downstream of the venous or arterial puncture cannula. These tube couplers are generally Luer lock couplers. If the tube coupler were to come loose, there would no longer be an access to the vessel. This situation too can be indicated by the device according to the invention and the method according to the invention.

In the device according to the invention and the method according to the invention, the AC voltage signal is injected and output relative to ground potential at any desired location of the arterial or venous blood conduit, i.e. either upstream or downstream of the tube coupler, for example a Luer lock coupler, i.e. in the tube portion between the inlet to the dialyzer, or outlet from the dialyzer, and the tube coupler, or in the tube portion between tube coupler and puncture cannula. If the AC voltage signal is injected and output in the tubular conduit portions between tube coupler and puncture cannula, only a slipping out of the puncture cannula can be indicated, not a faulty tube coupler. Indication of a faulty tube coupler requires that the injection or output takes place in a tubular conduit portion between dialyzer and tube coupler.

BRIEF DESCRIPTION OF THE DRAWINGS

Illustrative embodiments of the invention are explained in greater detail below with reference to the drawings, in which.

DETAILED DESCRIPTION OF THE DRAWINGS

Figure 1:
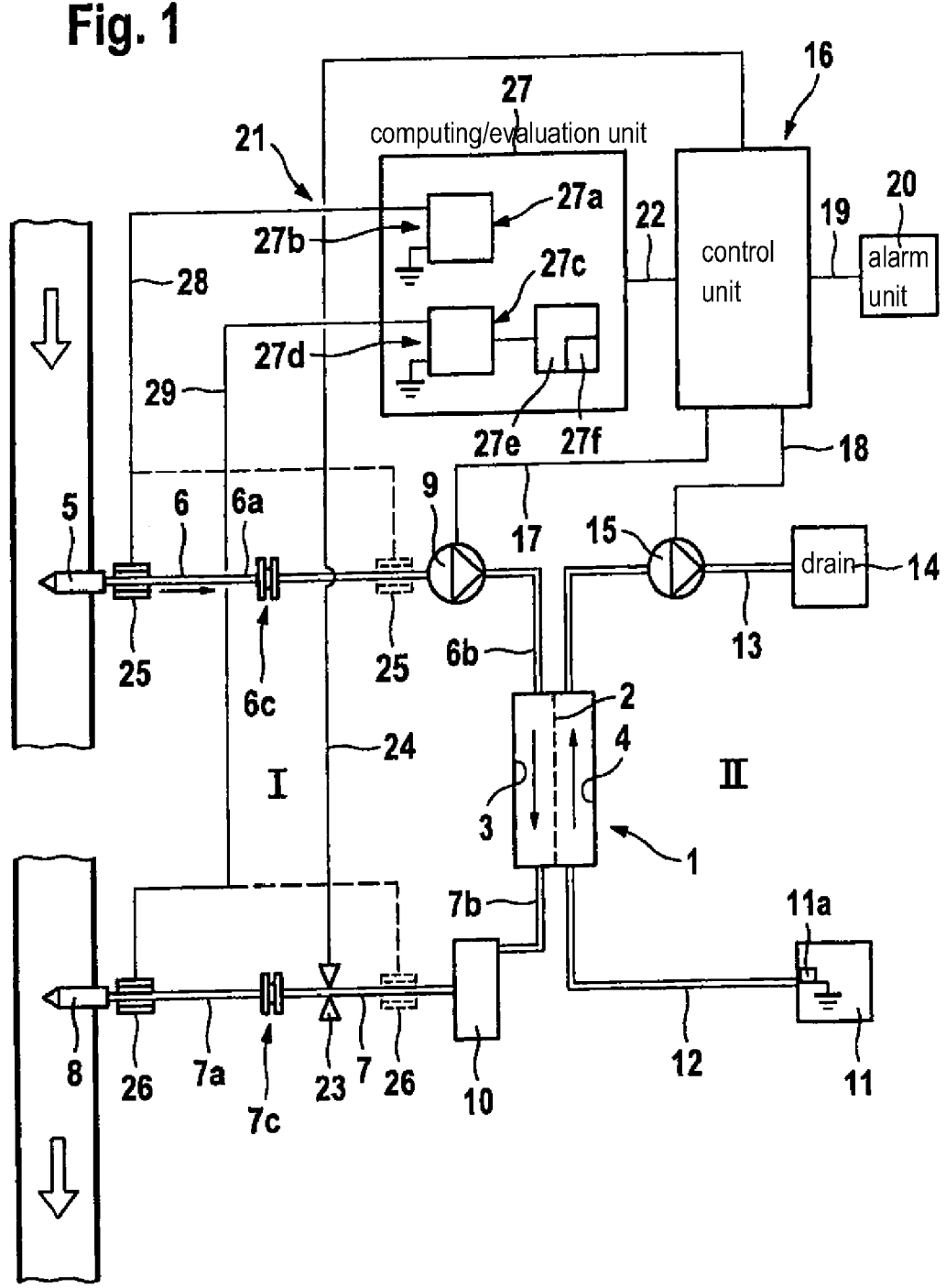
FIG. 1 shows the main components of a blood treatment device, together with a device for monitoring the patient access, in a greatly simplified schematic representation.

FIG. 1 shows the main components of a blood treatment device, for example a hemodialysis device, which comprises a device for monitoring the arterial and venous vascular access. The hemodialysis device has a dialyzer 1 which is divided by a semipermeable membrane 2 into a blood chamber 3 and a dialysis fluid chamber 4. An arterial tubular conduit 6 is connected to an artery of the patient by means of an arterial puncture cannula 5 and leads to the inlet of the blood chamber 3 of the dialyzer 1. Issuing from the outlet of the blood chamber 3 of the dialyzer 1, there is a venous tubular conduit 7 which is connected to a vein of the patient by means of a venous puncture cannula 8. The arterial tubular conduit 6 is routed into an occlusive blood pump 9 which conveys the blood in the extracorporeal blood circuit I. The venous tubular conduit 7 contains a bubble trap 10, for example a drip chamber, which holds back air bubbles in the blood.

The dialysis fluid circuit II of the hemodialysis device comprises a means 11 which is used to prepare the dialysis fluid and to which a dialysis fluid delivery line 12 is attached that leads to the inlet of the dialysis fluid chamber 4 of the dialyzer 1. Issuing from the outlet of the dialysis fluid chamber 4 of the dialyzer 1, there is a dialysis fluid discharge line 13 that leads to a drain 14. A dialysis fluid pump 15 is coupled into the dialysis fluid discharge line 13.

The arterial and venous tubular conduits 6, 7 are part of a tube set, the arterial and venous tubular conduits each having two tubular conduit portions 6a, 6b and 7a, 7b, respectively. The conduit portions 6a, 6b of the arterial tubular conduit 6 and the conduit portions 7a, 7b of the venous tubular conduit 7 are connected to one another by tube couplers 6c, 7c, for example Luer lock couplers, so that the tube portions towards the patient can be separated from the rest of the conduit portions of the tube set.

The dialysis device is controlled by a central control unit 16 which regulates the blood pump 9 and dialysis fluid pump 15 via control lines 17, 18, respectively. The central control unit 16 is connected by a data link 19 to an alarm unit 20, which emits an optical and/or acoustic alarm if a fault occurs.

A correct vascular access presupposes that both the arterial and venous puncture cannulas 5, 8 are located in the vessel. A correct vascular access also presupposes that the tube couplers 6c, 7c of the arterial and venous tubular conduits 6, 7 connect the two tubular conduit portions to one another.

For monitoring the vascular access, the dialysis device comprises a monitoring device 21 which communicates with the control unit 16 via a data link 22. The structure and the mode of operation of the monitoring device 21 will be described in detail below. The monitoring device 21 reports an incorrect vascular access to the control unit 16 via a data link 22, so that the control unit 16 activates the alarm unit 20, which emits an optical and/or acoustic alarm. Moreover, the control unit 16 closes a venous tube clamp 23 which is arranged on the venous tubular conduit 7 downstream of the blood chamber 3 of the dialyzer 1 and which is connected to the control unit 16 via a control link 24.

The monitoring device 21 has means 25 for capacitive injection of an AC voltage signal, and means 26 for capacitive output of an AC voltage signal, and also a computing and evaluation unit 27. The means for capacitive injection and output of the AC voltage signal are metal sleeves enclosing the tubular conduits.

In the illustrative embodiment according to FIG. 1, the arterial metal sleeve 25 encloses the arterial tubular conduit portion between arterial puncture cannula 5 and arterial tube coupler 6c, while the venous metal sleeve 26 encloses the venous tubular conduit portion between venous tube coupler 7c and venous puncture cannula 8. It is also possible, however, to arrange the arterial metal sleeve 25 in the arterial tubular conduit portion between the arterial tube coupler 6c and the blood chamber 3, preferably upstream of the blood pump 9, and to arrange the venous metal sleeve 26 in the venous tubular conduit portion between the blood chamber 3 and the venous tube coupler 7c, preferably upstream of the tube clamp 23. This arrangement is shown in FIG. 1 by broken lines.

The means 11 for preparation of the dialysis fluid ensures that the dialysis fluid is at ground potential, i.e. at the operational ground of the machine. For this purpose, the means 11 for preparing the dialysis fluid contains a symbolically indicated electrical contact element 11a, for example an grounding clip, which is in contact with the dialysis fluid. Since the dialysis fluid is in turn in contact with the blood via the membrane 2 of the dialyzer 1, the grounding of the dialysis fluid also means that the blood flowing through the tubular conduits 6, 7 is also connected to ground potential, i.e. connected to the operational ground of the machine.

The monitoring device 21 has means 27a for generating an AC voltage signal with a signal output 27b, one connector of the signal output being connected via an electrical connection line 28 to the arterial metal sleeve 25, while the other connector of the signal output is connected to ground potential, i.e. to the operational ground of the dialysis machine. In addition, the monitoring device has means 27c for measuring an AC voltage signal with a signal input 27d. One connector of the signal input 27d is connected via an electrical connection line 29 to the venous metal sleeve 26, while the other connector of the signal input is again connected to ground potential, i.e. to the operational ground of the machine.

In addition, the monitoring device 21 has means 27e for evaluating the AC voltage signal measured by the means 27c. The means 27e for evaluating the AC voltage signal in turn have means 27f for comparing the measured AC voltage signal to a predetermined limit value.

The monitoring device according to the present invention operates as follows. An AC voltage signal is generated which is capacitively injected into the extracorporeal blood circuit I on the arterial tubular conduit 6 and is capacitively output from the extracorporeal blood circuit I on the venous tubular conduit 7. The measured current flowing into the patient via the arterial or venous conduits upon application of the AC voltage signal is negligible. The amplitude of the output AC voltage signal is compared to a predetermined limit value. If the amplitude of the voltage signal is less than the predetermined limit value, the monitoring device 21 concludes there is an incorrect vascular access, emitting an alarm and interrupting the extracorporeal blood circuit.

FIGS. 2 to 5 show the electrical equivalent circuit diagrams of the dialysis device from FIG. 1, for different arrangements of the means for injection and output of the AC voltage signal.

In FIGS. 2 to 5, the individual components of the dialysis device are described by their impedance Z, which with discrete components can be represented as a series connection of a resistor Rb and a parallel connection of a resistor Ra and of a capacitor Cx. For the impedances of the individual components, the following abbreviations are used:
ZDD=Impedance: dialyzer, dialysate side
ZDB=Impedance: dialyzer, blood side
ZDDDB=Impedance: dialysate side→blood side
ZBSS=Impedance: blood tube segment
ZBF=Impedance: bubble trap
ZKA=Impedance: capacitive output
ZL=Impedance: tube coupler (Luer lock)
ZKE=Impedance: capacitive injection
ZPSS=Impedance: pump tube segment
ZSP=Impedance: shunt patient
ZPKTV=Impedance: venous puncture
ZPKTA=Impedance: arterial puncture Detachment of the arterial or venous puncture cannula 5, 8 signifies an interruption of the "electric circuit". Detachment of the arterial or venous tube coupler also signifies an interruption of the electric circuit. The interruption of the electric circuit results in an increase in the impedance, which is in turn reflected by a reduction in the amplitude of the measured AC voltage signal. The signal path between the injection location and output location is indicated in FIGS. 2 to 5 by a curved line.

Figure 2:
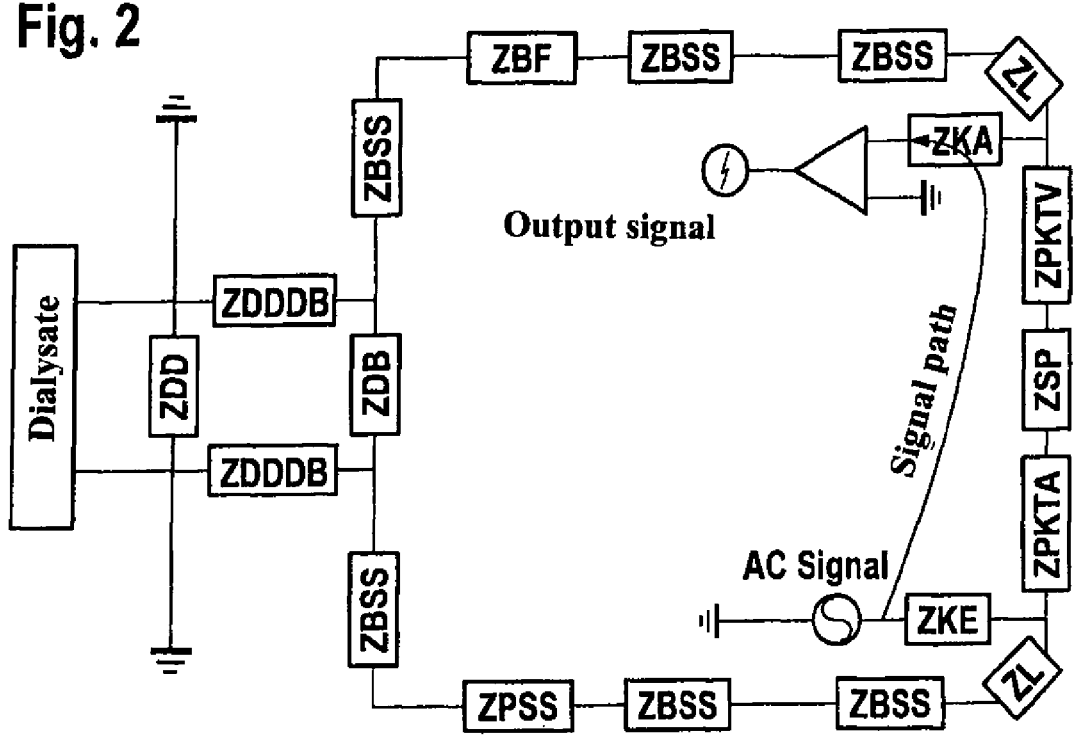
FIG. 2 shows the equivalent circuit diagram of the blood treatment device from FIG. 1.

FIG. 2 shows the arrangement, illustrated by solid lines in FIG. 1, of the metal sleeves 25, 26 for injection and output of the AC voltage signal. With this arrangement, only a disconnection or at least dislocation of the arterial and venous cannulas 5, 8 can be reliably indicated on the basis of a significant increase in impedance or reduction in the amplitude of the AC voltage signal, but not the detachment of the tube couplers.

Figure 3:
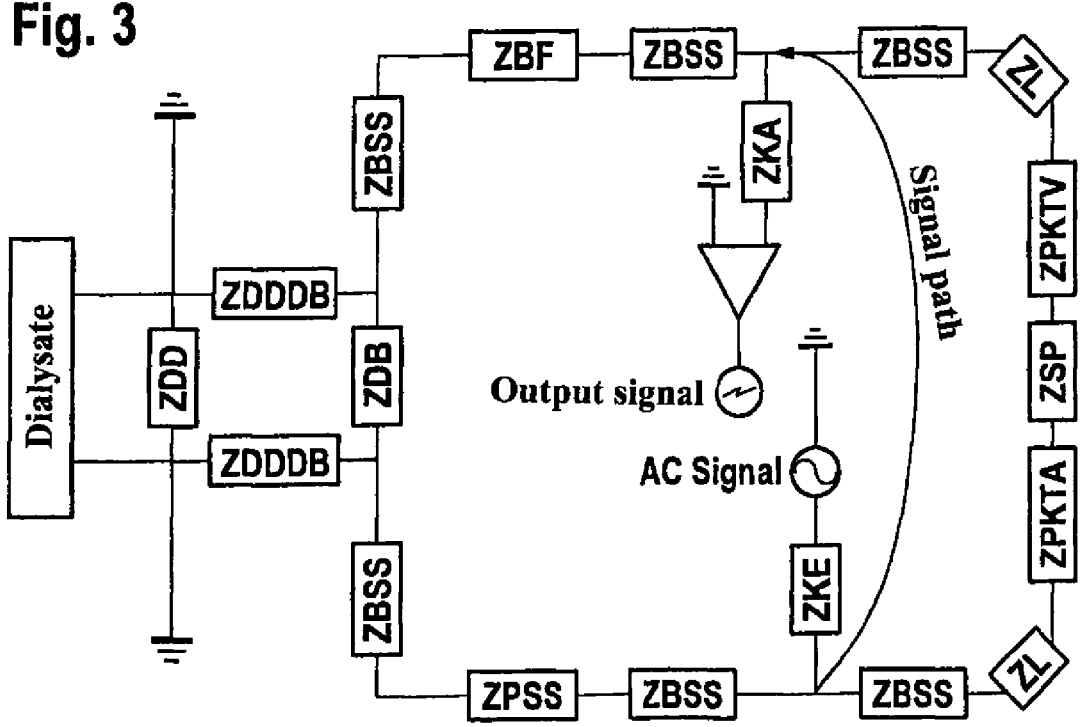
FIG. 3 shows the equivalent circuit diagram of an alternative embodiment of the blood treatment device, in which the AC voltage signal is injected downstream of an arterial tube coupler and the AC voltage signal is output upstream of a venous tube coupler, the arterial and venous tube couplers each connecting two tube portions of the arterial or venous tubular conduit.

FIG. 3 shows the arrangement, illustrated by broken lines in FIG. 1, of the arterial and venous metal sleeves 25, 26. With this arrangement, only a disconnection or at least dislocation of the arterial and venous cannulas 5, 8 can be reliably demonstrated on the basis of a significant increase in impedance or reduction in the amplitude of the AC voltage signal, but not the detachment of the tube couplers. By contrast, the detachment of a tube coupler leads only to a small signal rise, since there is no connection to ground through the impedance ZDDDB.

Figure 4:
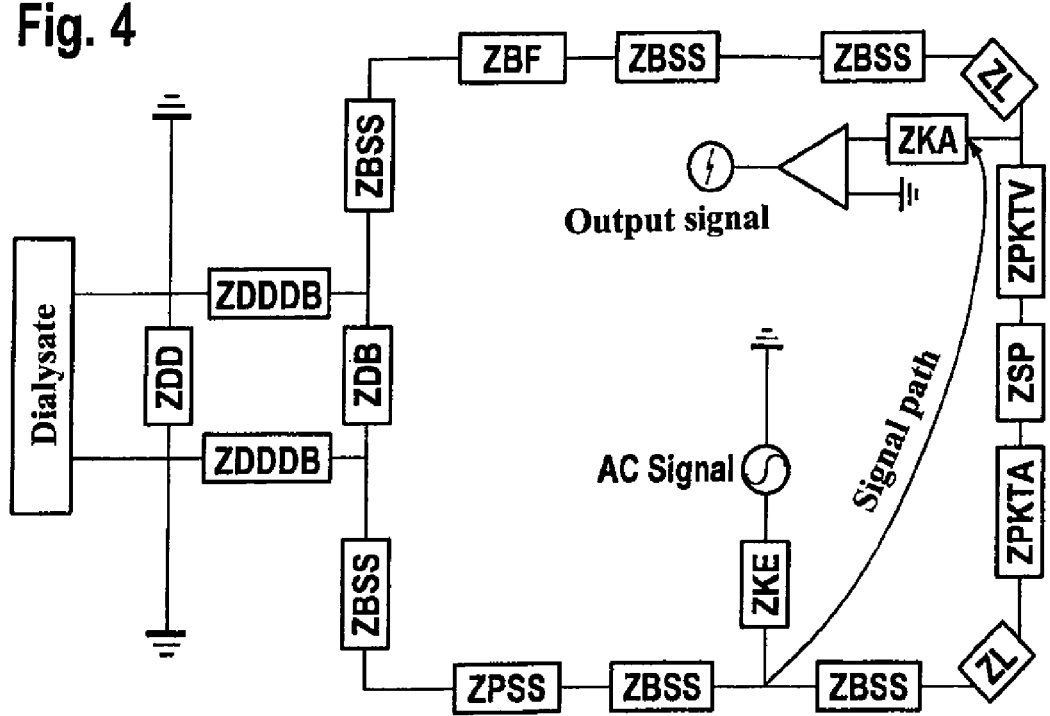
FIG. 4 shows another embodiment of the blood treatment device in which the AC voltage signal is injected downstream of the arterial tube coupler and the AC voltage signal is output downstream of the venous tube coupler.

FIG. 4 shows an illustrative embodiment in which the arterial metal sleeve 25 is arranged in the tubular conduit portion 6a of the arterial tubular conduit 6 between the blood chamber 3 and the arterial tube coupler 6c, while the venous metal sleeve 26 is arranged in the tubular conduit portion 7a of the venous tubular conduit 7 between the venous puncture cannula 8 and the venous tube coupler 7c (FIG. 1).

Figure 5:
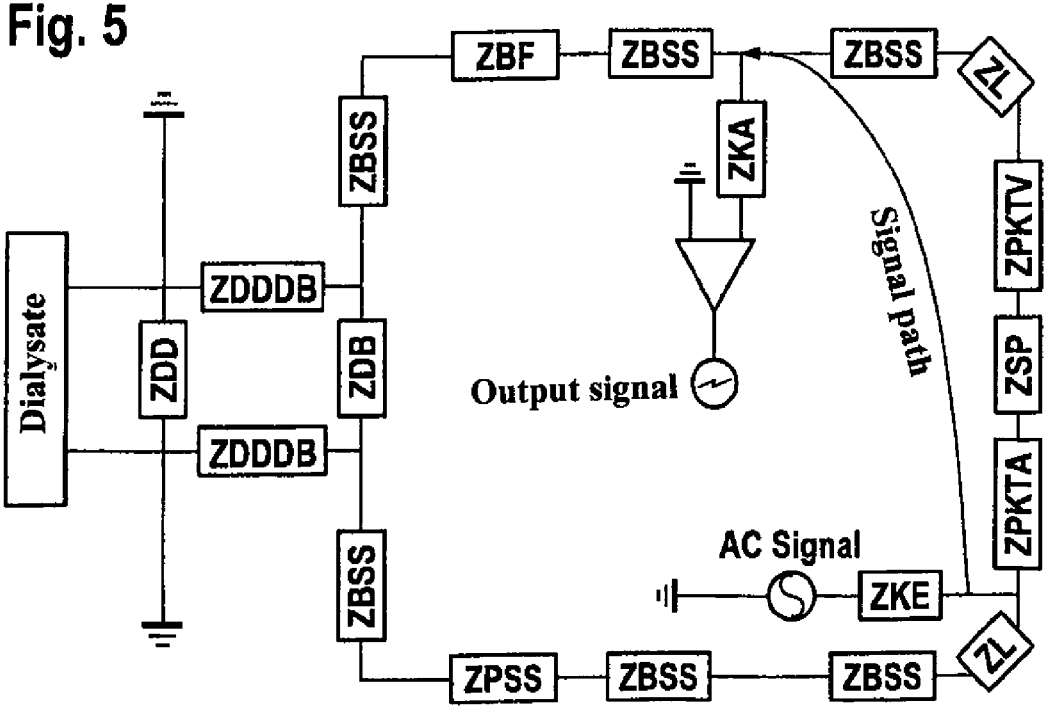
FIG. 5 shows another embodiment of the blood treatment device in which the AC voltage signal is injected upstream of the arterial tube coupler and the AC voltage signal is output upstream of the venous tube coupler.

FIG. 5 shows the arrangement of the arterial metal sleeve 25 in the arterial tubular conduit portion 6a between the arterial puncture cannula 5 and the arterial tube coupler 6c, while the venous metal sleeve 26 is arranged in the venous tubular conduit portion 7a between the blood chamber 3 and the venous tube coupler 7c.

In the illustrative embodiments according to FIGS. 4 and 5, detachment of the puncture cannulas 5, 8 and also of the tube couplers 6c, 7c is demonstrated by an increase in the impedance and a reduction in the amplitude of the measured AC voltage signal.

In the monitoring device according to the invention, the amplitude of the measured AC voltage signal can be compared not only to one predetermined reference value, but to several reference values. Therefore, with an appropriate arrangement of the injection site and output site, it is in principle possible to differentiate whether a puncture cannula or a tube coupler has come loose, since the respective fault is associated with a characteristic change in the impedance or signal amplitude. The extent of the significant change depends on the respective equivalent circuit diagram. Characteristic values can be established by comparative measurements.

The invention claimed is:
1. A monitoring device for monitoring an access to a patient, comprising:
  a first tubular conduit comprising a first patient connector for withdrawing a fluid;
  a second tubular conduit comprising a second patient connector for returning the fluid;
  an AC voltage signal generator comprising a signal output with a first output connector and second output connector;

a capacitive injection device for capacitive injection of the AC voltage signal at a first location of one of the first tubular conduit or the second tubular conduit;

a capacitive output device for capacitive output of the AC voltage signal at a second location of the other of the first tubular conduit or the second tubular conduit;

an AC voltage signal measuring device comprising a signal input with a first input connector and second input connector;

a first electrical connection between the first output connector of the signal output and the device for capacitive injection of the AC voltage signal, and a second electrical connection between the second output connector and a ground potential;

a third electrical connection between the fluid in the first tubular conduit and the second tubular conduit and the ground potential; and an AC voltage signal evaluating device, said evaluating device configured to interact with the AC voltage signal measuring device such that a characteristic change of the amplitude of the measured AC voltage signal points to an incorrect vascular access, wherein the first input connector is electrically connected to the capacitive output device, and the second input connector is electrically connected to the ground potential.

2. The monitoring device of claim 1, wherein the capacitive injection device comprises a first body of electrically conductive material enclosing one of the first tubular conduit or the second tubular conduit at the first location.

3. The monitoring device of claim 2, wherein the capacitive output device comprises a second body of electrically conductive material enclosing the other of the first tubular conduit or the second tubular conduit at the second location.

4. The monitoring device of claim 1, wherein the AC voltage signal evaluating device comprises:
an AC voltage signal comparing device configured to compare the measured AC voltage signal to a predetermined limit value, configured such that if the AC voltage signal is less than the limit value, this points to an incorrect vascular access.

5. The monitoring device of claim 1, wherein the monitoring device is configured to monitor a vascular access during an extracorporeal blood treatment, the first tubular conduit comprises an arterial tubular conduit, the first patient connector comprises an arterial puncture cannula, the second tubular connector comprises a venous tubular conduit, the second patient connector comprises a venous puncture cannula, and the fluid comprises blood.

6. A blood treatment device comprising:
the device of claim 5, and
a dialyzer divided by a semi-permeable membrane into a blood chamber and a dialysis fluid chamber, wherein the dialysis fluid chamber is part of a dialysis fluid circuit comprising a dialysis fluid, and the blood chamber is part of an extracorporeal blood circuit,
wherein the extracorporeal blood circuit comprises the arterial puncture cannula connected to the arterial tubular conduit leading to an inlet of the blood chamber of the dialyzer; and an outlet of the blood chamber leading to the venous tubular conduit connected to the venous puncture cannula.

7. The device of claim 6, wherein the third electrical connection between the fluid in the first tubular conduit and the second tubular conduit and the ground potential is arranged in the dialysis fluid circuit.

8. The device of claim 6, wherein the third electrical connection between the fluid in the first tubular conduit and the second tubular conduit and the ground potential is an electrical contact element that comes into contact with the dialysis fluid and is connected to the ground potential.

9. The device of claim 6, wherein the capacitive injection device is arranged downstream of the arterial puncture cannula at the first location of the arterial blood conduit.

10. The device of claim 6, further comprising an arterial tube coupler located in the arterial blood conduit downstream of the arterial puncture cannula, the arterial tube coupler defining a first portion of the arterial tubular conduit between the arterial tube coupler and the arterial puncture cannula, and a second portion of the arterial tubular conduit between the blood chamber and the arterial tube coupler.

11. The device of claim 10, wherein the capacitive injection device is arranged in the second portion of the arterial tubular conduit.

12. The device of claim 10, wherein the capacitive injection device is arranged in the first portion of the arterial tubular conduit.

13. The device of claim 6, wherein the capacitive output device is arranged upstream of the venous puncture cannula at the second location of the venous blood conduit.

14. The device of claim 6, further comprising a venous tube coupler located in the venous tubular conduit upstream of the venous puncture cannula, the venous tube coupler defining a first portion of the venous tubular conduit between the venous tubular coupler and the venous puncture cannula, and a second portion of the venous tubular conduit between the blood chamber and the venous tube coupler.

15. The device of claim 14, wherein the capacitive output device is arranged in the second portion of the venous blood conduit.

16. The device of claim 14, wherein the capacitive output device is arranged in the first portion of the venous tubular conduit.

17. A monitoring device for monitoring an access to a patient, comprising:
a first tubular conduit comprising a first patient connector configured to withdraw a fluid from said patient;
a second tubular conduit comprising a second patient connector configured to return the fluid to said patient;
an AC voltage signal generator comprising a signal output with a first output connector and second output connector;
a capacitive injection device configured for capacitive injection of the AC voltage signal, said capacitive injection device enclosing a first portion of one of the first tubular conduit or the second tubular conduit;
a capacitive output device configured for capacitive output of the AC voltage signal, said capacitive output device enclosing a second portion of the other of the first tubular conduit or the second tubular conduit;
an AC voltage signal measuring device comprising a signal input with a first input connector and second input connector;
a first electrical connection between the first output connector of the signal output and the device for capacitive injection of the AC voltage signal, and a second electrical connection between the second output connector and a ground potential;
a third electrical connection between the fluid in the first tubular conduit and the second tubular conduit and the ground potential; and
an AC voltage signal evaluating device, said evaluating device configured to interact with the AC voltage signal measuring device such that a characteristic change of the amplitude of the measured AC voltage signal points to an incorrect vascular access, wherein the first input connector is electrically connected to the capacitive output device, and the second input connector is electrically connected to the ground potential.

18. The monitoring device of claim 17, wherein the capacitive injection device comprises a first body of electrically conductive material enclosing one of the first tubular conduit or the second tubular conduit at the first portion.

19. The monitoring device of claim 18, wherein the capacitive output device comprises a second body of electrically conductive material enclosing the other of the first tubular conduit or the second tubular conduit at the second portion.

20. The monitoring device of claim 17, wherein the AC voltage signal evaluating device comprises:

an AC voltage signal comparing device configured to compare the measured AC voltage signal to a predetermined limit value, configured such that if the AC voltage signal is less than the limit value, this points to an incorrect vascular access.

* * * * *